United States Patent [19]

Sokol et al.

[11] Patent Number: 5,401,652

[45] Date of Patent: Mar. 28, 1995

[54] NUCLEIC ACID SEQUENCE ENCODING APAMIN RECEPTOR PROTEIN

[75] Inventors: Patricia T. Sokol, Bedminster; Mohammad R. Ziai, Montvale, both of N.J.

[73] Assignee: American Cyanamid Company, Wayne, N.J.

[21] Appl. No.: 923,095

[22] Filed: Jul. 30, 1992

[51] Int. Cl.$^6$ .................. C12N 15/70; C12N 5/10; C12N 1/15; C07H 21/04

[52] U.S. Cl. .................. 435/240.2; 536/23.5; 536/24.31; 435/252.3; 435/320.1; 435/6; 935/6; 935/22; 935/66; 935/70

[58] Field of Search .................. 536/23.5, 24.31; 435/69.1, 252.1, 252.3, 320.1, 6, 240.2; 514/44

[56] References Cited

PUBLICATIONS

Rudy, B., "Diversity and Ubiquity of K Channels, Neuroscience", 25:729–749, 1988.
Castle, N. A., et al., "Toxins in the characterization of potassium channels":, TINS, 12:59–65, 1989.
Haylett, B. G. et al., "Calcium-activated potassium channels", In Cook, N. S. (ed.), Ellis Horwood Ltd., 70–95, 1990.
Latorre, R. et al., "Varieties of Calcium-Activated Potassium Channels", Annu. Rev. Physiol., 51:385–399, 1989.
Pennefather, P. et al., "Two distinct Ca-dependent K currents in bullfrog sympathetic ganglion cells", Proc. Natl. Acad. Sci., USA, 82:3040–3044, 1985.
Marty A., "The physiological role of calcium-dependent channels":, TINS, 12:420–424.
Lancaster, B., et al., "Calcium Activates Two Types of Potassium Channels in Rat Hippocampal Neurons in Culture", J. Neurosci., 11:23–30, 1991.
Strong, P. N., "Potassium Channel Toxins", Pharmac. Ther., 46:137–162, 1990.
Saunders, H. H. et al., "Spontaneous Transient Outward Currents and CA++—Activated K+ Channels in Swine Tracheal Smooth Muscle Cells.", J. Pharmacol. Exp. Ther. 257:1114–1119, 1991.
Moczydlowski, E. et al., "An Emerging Pharmacology of Peptide Toxins Targeted Against Potassium Channels", J. Membrane Biol., 105:95–111, 1988.
Blatz, A. L. et al., "Ion Conductance and Selectivity of Single Calcium-activated Potassium Channels in Cultured Rat Muscle", J. Gen. Physiol., 84:1–23, 1984.
Blatz, A. L. et al., "Single apamin-blocked Ca-activated K+ channels of small conductance in cultured rat skeletal muscle", Nature, 323:718–720, 1986.
Blatz, A. L. et al., "Calcium-activated potassium channels" TINS, 10:463–467, 1987.
Habermann, E., et al., "Bee Venom Neurotoxin (Apamin): Iodine Labeling and Characterization of Binding Sites", Eur. J. Biochem. 94:355–364, 1979.
Mourre, C. et al., Quantitative Autoradiographic Mapping in Rat Brain of the Receptor of Apamin, a Polypeptide Toxin Specific for One Class of CA2+--Dependent K+ Channels Brain Res., 382:239–249, 1986.
Seagar, M. J. et al., "Molecular Structure of Rat Brain Apamin Receptor: Differential Photoaffinity Labeling of Putative K+ Channel Subunits and Target Size Analysis" Biochemistry, 25:4051–4057, 1986.
Seagar, M. J. et al., "Solubilization of the Apamin Receptor Associated with a Calcium-Activated Potassium Channel From Rat Brain", J. Neurosci., 7:565–570, 1987.
Schmid-Antomarchi, H. et al., "Molecular properties of the apamin-binding component of the CA2+-–dependent K+ channel" Eur. J. Biochem., 142:1–6, 1984.

(List continued on next page.)

Primary Examiner—Margaret Parr
Assistant Examiner—Carla Myers
Attorney, Agent, or Firm—Hamilton, Brook, Smith & Reynolds

[57] ABSTRACT

The present invention relates to an isolated nucleic acid fragment comprising a nucleic acid sequence encoding an apamin receptor protein, or biologically active fragment thereof.

8 Claims, 9 Drawing Sheets

PUBLICATIONS

Wu, K. et al. "Existence of a CA2+−Dependent K+ Channel in Synaptic Membrane and Postsynaptic Density Fractions Isolated from Canine Cerebral Cortex and Cerebellum, as Determined by Apamin Binding", Brain Res., 360:183–194, 1985.

Seagar, M. J. et al., "Photoaffinity Labeling of Components of the Apamin-sensitive K+ Channel in Neuronal Membranes", J. Biol. Chem., 260:3895–3898, 1985.

Leveque, C. et al., "Polypeptide components of the apamin receptor associated with a calcium activated potassium channel", FEBS Letters, 275:185–189, 1990.

Marqueze, B. et al., "Photoaffinity labeling of the K+−channel associated apamin-binding molecule in smooth muscle, liver and heart membranes", 169:295–298, 1987.

Ziai, M. R. et al., "Analysis with Monoclonal Antibodies of the Molecular and Cellular Heterogeneity of Human High Molecular Weight Melanoma Associated Antigen", Cancer Res. 47:2474–2480, 1987.

Ziai, M. R. et al., "an Enzynme-Linked Double Antibody Immunoassay to Measure Muring Immunoglobulins-Its Application to Determin the Specific Activity of Radiolabeled Monoclonal Antibodies", J. Immunoassay, 11:89–95, 1990.

Hayashibe, K. et al., "A Heterogeneous Double Antibody Enzyme-Linked Immunoassay to Measure β-Galactosidase Fusion Protein", 11:89–95, 1990.

Staros, J. V. et al. "Enahncement by N−Hydroxysulfosucinimide of Water-Soluble Carbodimide-Mediated Coupling Reactions", Analyt. Biochem., 156:220–222, 1986.

Cornett, W. C. et al., "Specificity of Monoclonal Antibodies Reactive with Fusobacterium nucleatum: Effect of Formalin Fixation", J. Immunol Methods, 84:321–326, 1985.

Lu et al., "CA2+−activated K+ Channels from Rabbit Kidney Medullary Thick Ascending Limb Cells Expressed in Xenopus Oocytes", J. Biol. Chem. 265:16190–16194, 1990.

Wang, W., "Renal Potassium Channels and their Regulation" Annu. Rev. Physiol., 54:81–96, 1992.

Atkinson, N. S. et al., "A Component of Calcium-Activated Potassium Channels Encoded by the Drosophila Slo Locus", Science, 253:551–555, 1991.

Daniel, S. et al., "Screening for Potassium Channel Modulators by a High Through-Put 86-Rubidium Efflux Assay in a 96-Well Microtiter Plate", J. Pharmacol Methods, 25:185–193, 1991.

Messier, C., "Effect of apamin, a toxin that inhibits CA2+−dependent K+ channels, on learning and memory processes", Brain Res., 551:322–326, 1991.

Lee et al Science (1988) 239:1288–1291.

Leveque et al FEBS Letters (1990) 275:185–189.

Fosset et al Proc Natl Acad Sci, USA (1984) 81:7228–7232.

Sambrook et al, Molecular Cloning: A Laboratory Manual (1989) Cold Spring Harbor Laboratory Press, pp. 16.3–16.40.

```
    agcagctccataggcccagccccggcgtacaaggatcacttccggtggtacttcactacc
1   ------------+---------+---------+---------+---------+---------+ 60
    tcgtcgaggtatccgggtcggggccgcatgttcctagtgaaggccaccatgaagtgatgg aagaagctgcgattgggcgagcgtggaaggggcatttccggtgtccacctgcttgggttc
61  ------------+---------+---------+---------+---------+---------+ 120
    ttcttcgacgctaacccgctcgcaccttccccgtaaaggccacaggtggacgaacccaag tttggacagaagtaggaagATGGAGCTCGGCGCCGCGGCCCGTGCTTGGTCGCTCTTGTG
121 ------------+---------+---------+---------+---------+---------+ 180
    aaacctgtcttcatccttcTACCTCGAGCCGCGGCGCCGGGCACGAACCAGCGAGAACAC

M  E  L  G  A  A  A  R  A  W  S  L  L  W

GCTGCTGCTTCCCTTGCTTGGCCTGGTCGGCGCCAGCGGTCCCCGTACCTTAGTGCTTCT
181 ------------+---------+---------+---------+---------+---------+ 240
    CGACGACGAAGGGAACGAACCGGACCAGCCGCGGTCGCCAGGGGCATGGAATCACGAAGA

L  L  L  P  L  L  G  L  V  G  A  S  G  P  R  T  L  V  L  L

GGACAACCTCAACCTGCGGGAGACGCATTCACTTTTCTTCCGGAGCCTAAAGGATCGGGG
241 ------------+---------+---------+---------+---------+---------+ 300
    CCTGTTGGAGTTGGACGCCCTCTGCGTAAGTGAAAAGAAGGCCTCGGATTTCCTAGCCCC

D  N  L  N  L  R  E  T  H  S  L  F  F  R  S  L  K  D  R  G

CTTCGTACTCACATTCAAGACCGCAGATGACCCCAGCCTGTCCCTGATTAAGTACGGAGA
301 ------------+---------+---------+---------+---------+---------+ 360
    GAAGCATGAGTGTAAGTTCTGGCGTCTACTGGGGTCGGACAGGGACTAATTCATGCCTCT

```
        GTTCCTCTATGACAATCTCATCGTCTTTTCACCTTCGGTAGAAGATTTTGGAGGAAATAT
361     ---------+---------+---------+---------+---------+---------+   420
        CAAGGAGATACTGTTAGAGTAGCAGAAAAGTGGAAGCCATCTTCTAAAACCTCCTTTATA

F  L  Y  D  N  L  I  V  F  S  P  S  V  E  D  F  G  G  N  I

CAACGTGGAGACCATCAGTACCTTTATCGACGGCGGAGGCAGTGTCCTGGTAGCTGCCAG
421     ---------+---------+---------+---------+---------+---------+   480
        GTTGCACCTCTGGTAGTCATGGAAATAGCTGCCGCCTCCGTCACAGGACCATCGACGGTC

N  V  E  T  I  S  T  F  I  D  G  G  G  S  V  L  V  A  A  S

CTCAGACATCGGTGACCCTCTCCGCGAGCTGGGCAGTGAGTGTGGGATTGAGTTTGACGA
481     ---------+---------+---------+---------+---------+---------+   540
        GAGTCTGTAGCCACTGGGAGAGGCGCTCGACCCGTCACTCACACCCTAACTCAAACTGCT
                                              *        *     *
         S  D  I  G  D  P  L  R  E  L  G  S  E  C  G  I  E  F  D  E

GGAGAAAACGGCCGTCATTGACCATCACAACTATGATGTCTCAGACCTCGGCCAGCACAC
541     ---------+---------+---------+---------+---------+---------+   600
        CCTCTTTTGCCGGCAGTAACTGGTAGTGTTGATACTACAGAGTCTGGAGCCGGTCGTGTG
           *  *
         E  K  T  A  V  I  D  H  H  N  Y  D  V  S  D  L  G  Q  H  T

GCTCATTGTGGCCGACACTGAGAACCTGCTGAAGGCCCCGACCATCGTCGGGAAGTCATC
601     ---------+---------+---------+---------+---------+---------+   660
        CGAGTAACACCGGCTGTGACTCTTGGACGACTTCCGGGGCTGGTAGCAGCCCTTCAGTAG

```
       TCTGAATCCCATCCTCTTCCGAGGTGTTGGGATGGTGGCTGATCCTGACAATCCTTTGGT
661    ----------+----------+----------+----------+----------+----------+  720
       AGACTTAGGGTAGGAGAAGGCTCCACAACCCTACCACCGACTAGGACTGTTAGGAAACCA

L  N  P  I  L  F  R  G  V  G  M  V  A  D  P  D  N  P  L  V
        ‾‾‾‾‾‾‾‾‾‾‾‾‾‾‾‾‾‾‾‾‾‾‾‾‾‾‾‾‾‾‾‾

GCTGGACATCCTGACCGGCTCTTCTACCTCTTACTCCTTCTTCCCAGATAAACCCATCAC
721    ----------+----------+----------+----------+----------+----------+  780
       CGACCTGTAGGACTGGCCGAGAAGATGGAGAATGAGGAAGAAGGGTCTATTTGGGTAGTG

L  D  I  L  T  G  S  S  T  S  Y  S  F  F  P  D  K  P  I  T

GCAGTACCCGCACGCGGTGGGGAAGAACACGCTGCTCATCGCGGGGCTGCAGGCCCGGAA
781    ----------+----------+----------+----------+----------+----------+  840
       CGTCATGGGCGTGCGCCACCCCTTCTTGTGCGACGAGTAGCGCCCCGACGTCCGGGCCTT

Q  Y  P  H  A  V  G  K  N  T  L  L  I  A  G  L  Q  A  R  N

CAACGCCCGTGTCATCTTCAGCGGCTCCCTCGACTTCTTCAGCGATGCCTTCTTCAACTC
841    ----------+----------+----------+----------+----------+----------+  900
       GTTGCGGGCACAGTAGAAGTCGCCGAGGGAGCTGAAGAAGTCGCTACGGAAGAAGTTGAG

N  A  R  V  I  F  S  G  S  L  D  F  F  S  D  A  F  F  N  S
              ‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾

CGCGGTGCAGAAGGCCACGCCTGGCTCCCAGAGGTATCCCCAGACAGGCAACTATGAGCT
901    ----------+----------+----------+----------+----------+----------+  960
       GCGCCACGTCTTCCGGTGCGGACCGAGGGTCTCCATAGGGGTCTGTCCGTTGATACTCGA

A  V  Q  K  A  T  P  G (S  Q  R) Y  P  Q  T  G  N  Y  E  L
        ‾‾‾‾

CGCCGTGGCCCTCTCCCGCTGGGTGTTCAAGGAGGAGGGTGTCCTCCGAGTGGGGCCTGT
961    ----------+----------+----------+----------+----------+----------+  1020
       GCGGCACCGGGAGAGGGCGACCCACAAGTTCCTCCTCCCACAGGAGGCTCACCCCGGACA

```
         GTCCCACCATCGGGTGGGCGAGAAAGCCCCACCCAACGCCTACACCGTCACTGACCTAGT
1021     ---------+---------+---------+---------+---------+---------+  1080
         CAGGGTGGTAGCCCACCCGCTCTTTCGGGGTGGGTTGCGGATGTGGCAGTGACTGGATCA

S  H  H  R  V  G  E  K  A  P  P  N  A  Y  T  V  T  D  L  V

CGAGTACAGCATCGTGATTGAGCAGCTCTCACAGGGCAGATGGGTCCCCTTTGATGGCGA
1081     ---------+---------+---------+---------+---------+---------+  1140
         GCTCATGTCGTAGCACTAACTCGTCGAGAGTGTCCCGTCTACCCAGGGGAAACTACCGCT

E  Y  S  I  V  I  E  Q  L  S  Q  G  R  W  V  P  F  D  G  D

CGACATTCAGCTGGAGTTTGTCCGCATCGATCCTTTCGTGAGGACCTTCTTGAAGAGGAA
1141     ---------+---------+---------+---------+---------+---------+  1200
         GCTGTAAGTCGACCTCAAACAGGCGTAGCTAGGAAAGCACTCCTGGAAGAACTTCTCCTT

D  I  Q  L  E  F  V  R  I  D  P  F  V  R  T  F  L  K  R  K

AGGCGGCAAGTACAGCGTCCAGTTCAAGTTGCCGGACGTGTACGGCGTGTTCCAGTTCAA
1201     ---------+---------+---------+---------+---------+---------+  1260
         TCCGCCGTTCATGTCGCAGGTCAAGTTCAACGGCCTGCACATGCCGCACAAGGTCAAGTT

G  G  K  Y  S  V  Q  F  K  L  P  D  V  Y  G  V  F  Q  F  K

AGTGGACTACAACCGGCTGGGCTACACGCACCTGTACTCCTCCACTCAGGTGTCCGTGCG
1261     ---------+---------+---------+---------+---------+---------+  1320
         TCACCTGATGTTGGCCGACCCGATGTGCGTGGACATGAGGAGGTGAGTCCACAGGCACGC

V  D  Y  N  R  L  G  Y  T  H  L  Y  S  S  T  Q  V  S  V  R

GCCCCTGCAGGCACACGCAGTACGAGCGCTTCATCCCCTCGGCTTACCCCTACTACGCCA
1321     ---------+---------+---------+---------+---------+---------+  1380
         CGGGGACGTCCGTGTGCGTCATGCTCGCGAAGTAGGGGAGCCGAATGGGGATGATGCGGT

```
            GCGCCTTCTCCATGATGGTCGGGCTCTTCATCTTCAGCGTCGTCTTCTTGCACATGAAGG
     1381  ------------+----------+----------+----------+----------+----------+  1440
            CGCGGAAGAGGTACTACCAGCCCGAGAAGTAGAAGTCGCAGCAGAAGAACGTGTACTTCC

R [L] L H D G R A [L] H L Q R R L [L] A H E G

AGAAGGAGAAGTCTGActgaggggccgggccgggccccaggactccttacaacacacagg
     1441  ------------+----------+----------+----------+----------+----------+  1500
            TCTTCCTCTTCAGACTgactccccggcccggcccggggtcctgaggaatgttgtgtgtcc

E G E V * gagggttttttataggcttgccttccccccccctttatggtgggctttgtttgttttttaaag
     1501  ------------+----------+----------+----------+----------+----------+  1560
            ctcccaaaaatatccgaacggaaggggggggaaataccacccgaaacaaacaaaaatttc ccacggacaatggcacagcttacctcagtgggagatgcaagatgagtaccaggggggtggt
     1561  ------------+----------+----------+----------+----------+----------+  1620
            ggtgcctgttaccgtgtcgaatggagtcaccctctacgttctactcatggtcccccacca taggaataatttctaagttttttccaccttgaatgctgagtggtattttttcatatgtaaag
     1621  ------------+----------+----------+----------+----------+----------+  1680
            atccttattaaagattcaaaaaggtggaacttacgactcaccataaaaagtatacatttc tcaactgatttctaaaataaaagaaaaaacatcaccctcagaaaaaaaaaa
     1681  ------------+----------+----------+----------+----------+  1730
            agttgactaaagattttatttttcttttttgtagtgggagtctttttttttt
```

NUCLEIC ACID SEQUENCE ENCODING APAMIN RECEPTOR PROTEIN

Potassium (K) channels are integral membrane proteins of great molecular and functional diversity, present in practically all mammalian cells. These channels are primarily responsible for maintaining a resting membrane potential and are rapidly activated in response to an external depolarizing stimulus, binding of certain ligands, or changes in the intracellular concentration of calcium or ATP. In the excitable cells such as neurons or cardiac myocytes, K-channels determine the duration of the action potential thus performing a vital function in the CNS and the cardiac functions (reviewed in 1–2) The calcium-activated K-channel sub-family consists of at least three discernible ionic currents; a large ("BK"), an intermediate ("IK") and a small conductance ("SK") channels (Reviewed in 3–5). These K-channels are activated in response to a rise in the intracellular concentration of calcium $[Ca^{2+}]i$. In addition to $[Ca^{2+}]i$, the "BK" and "IK" channels are also sensitive to the changes in the membrane potential, whereas "SK" channel has no significant voltage sensitivity.

Functionally, the SK-channel is involved in the after-hyperpolarization that follows action potentials in many neurons. These include the sympathetic ganglionic neurons, hippocampal neurons, neurosecretory neurons and spinal moroneurons, as well as the skeletal muscle cells (1, 5–9). Furthermore, the SK-channel has been suggested to play a major role in the spontaneous transient outward currents in the tracheal smooth muscle cells (10), the inhibitory action of the $\alpha_1$-adrenoceptors, neurotensin receptor and the P2-subtype of the ATP receptor (4, 9).

The neuronal and the skeletal muscle SK-channel is specifically and avidly blocked by a bee venom-derived peptide toxin, apamin (5, 11–14). By all indications, the apamin receptor complex is either identical to, or closely associated with the SK-channel. Apamin is an 18 amino acid neurotoxic peptide which has a single class of binding sites in the rat brain synaptosomes and brain slices with an apparent dissociation constant ($K_d$) of 10–25 pM (15, 16). Apamin is also capable of a temperature dependent and high affinity ($K_d$=30–150 pM) binding to the detergent solubilized brain receptor sites (17–20). The reported $B_{max}$ value for the rat brain synaptosomes and brain slices is 10–30 fmol/mg protein (16, 17, 20), while that for the detergent solubilized receptor ranges from 0.45 to 17 fmol/mg protein (18, 19).

The polypeptide components of the apamin receptor have been studied by several groups. Cross-linking experiments using [$^{125}$I]apamin, followed by SDS-PAGE and autoradiography have indicated that the apamin binding proteins of the rat brain synaptosomal membrane consist of two protein species, a major 80–86 KDa protein and, in most reported preparations, a minor 50–59 KDa band (17, 21, 22). Partial peptide mapping of the two protein bands, using an anti-apamin anti-serum, has shown that the smaller polypeptide is likely to be a proteolytic fragment of the larger protein and not an additional subunit of the apamin binding protein in the brain. Furthermore, in the plasma membrane of the cultured neurons or astrocytes, there are additional components with the ability to cross-link to [$^{125}$I]apamin. Cross-linking of [$^{125}$I]apamin to the membranes from the rat heart, liver and smooth muscle has also indicated that a 85–87 KDa polypeptide is the major labeled component of the apamin binding complex (23). A second 59 KDa protein was identified in the liver membrane only (23).

The blocking of the small conductance calcium 1 U activated potassium channel (sKca) results in prolongation of the action potential, while its activation by an increase in the intracellular calcium concentration accelerates the rate of hyperpolarization, thus shortening the duration of the action potential. In vascular smooth muscle cells (such as those in veins and arteries), activation of sKca results in the hyperpolarization of the smooth muscle membrane, which in turn results in the inhibition of the voltage-gated calcium channels. The inhibition of the latter may then lead to the relaxation of the blood vessels and lowering of the blood pressure. In the heart, modulation of sKca can be a potentially useful means to regulate an arrhythmic heart. In the nervous system, the hippocampus of Alzheimer's patients shows a drastic reduction in apamin denisty (30). Further apamin receptor in neurons has been reported to be involved in the process of learning and memory (42). Thus, manipulation of this receptor may also result in improving cognition. Notwithstanding the significant therapeutic potential manipulation of sKca may have, relatively little is known about the identity of the proteins involved in this channel. The present invention now provides a key element in the study of the potassium channel function.

SUMMARY OF THE INVENTION

Figure 3A:
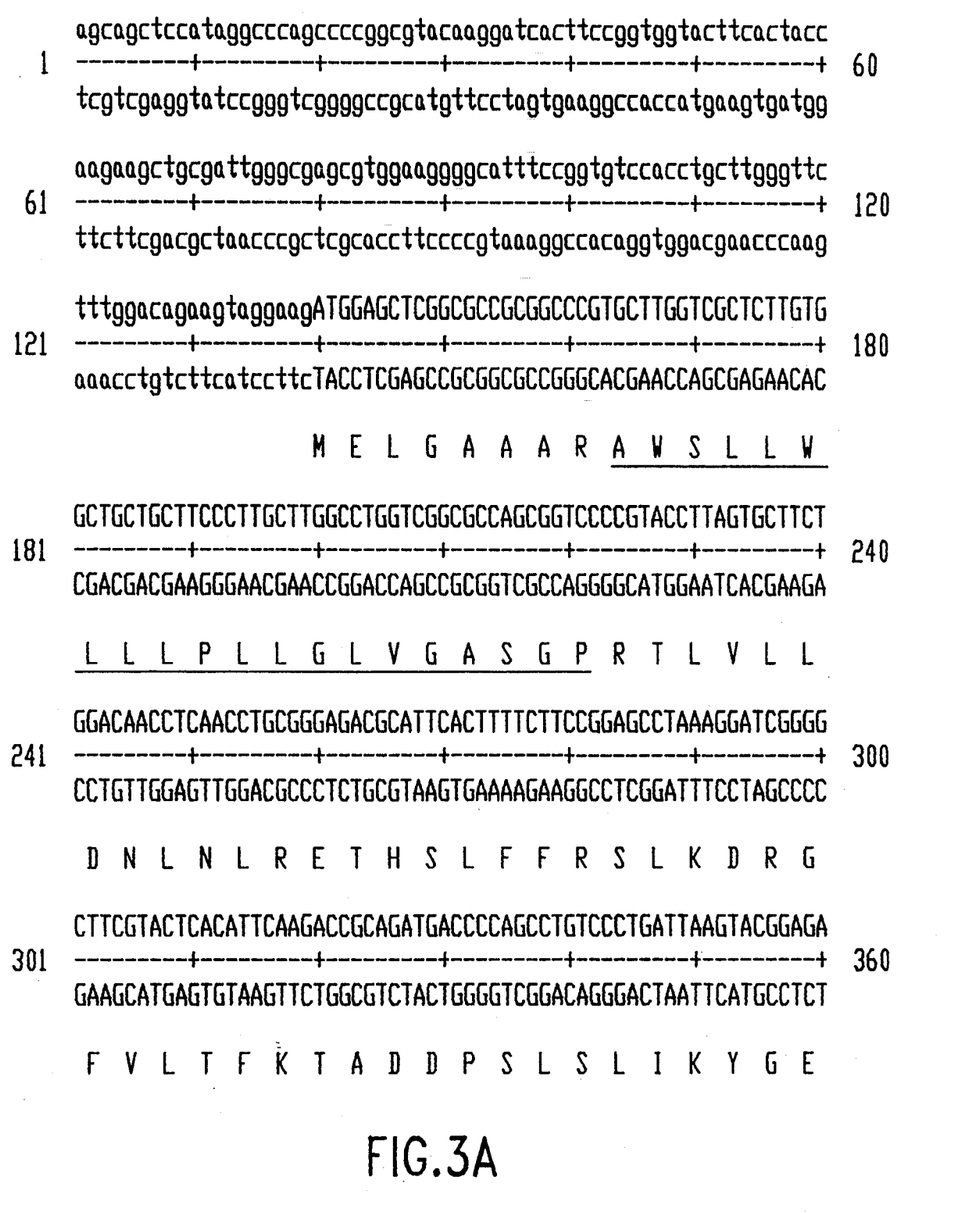
Figure 3B:
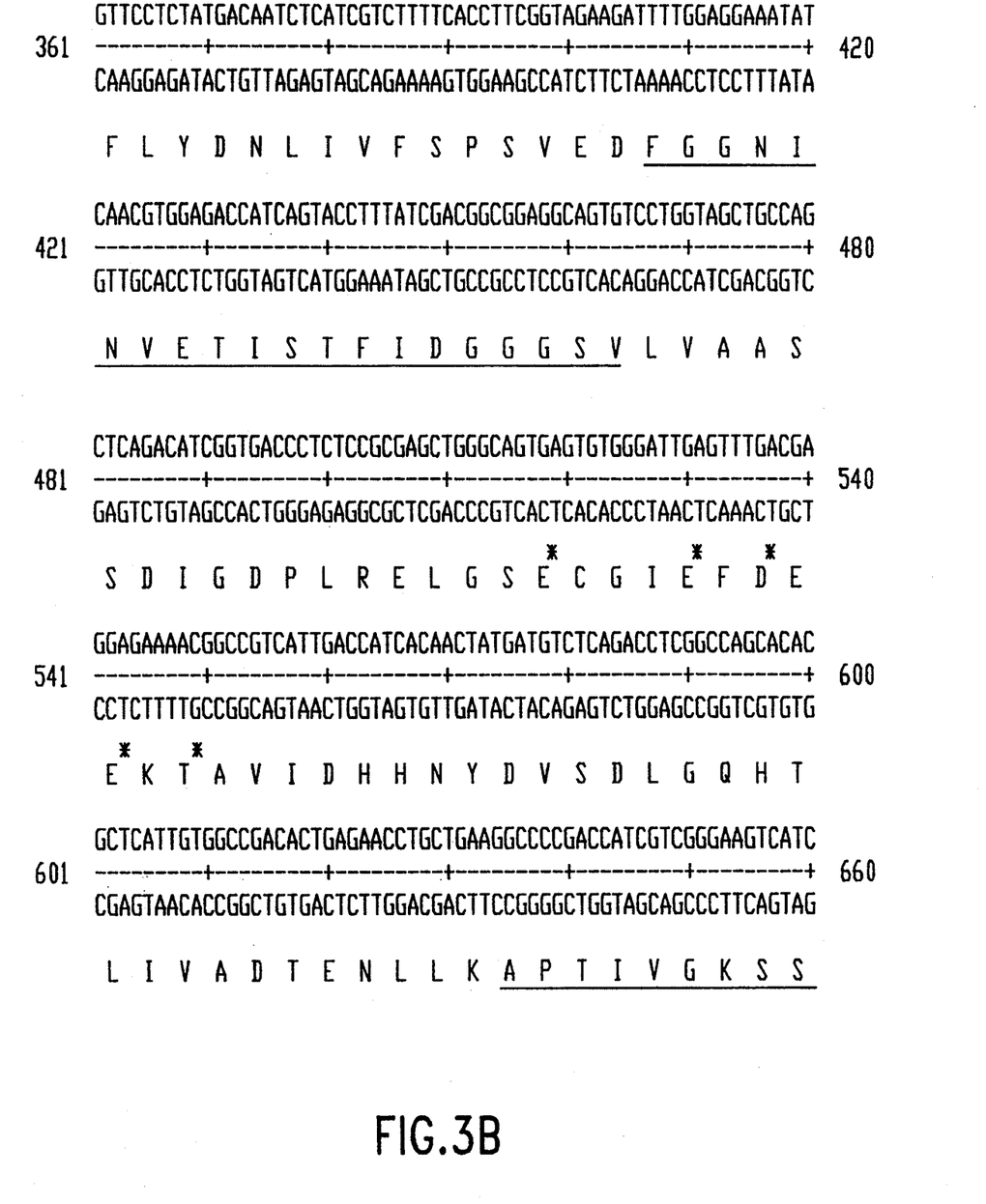
Figure 3C:
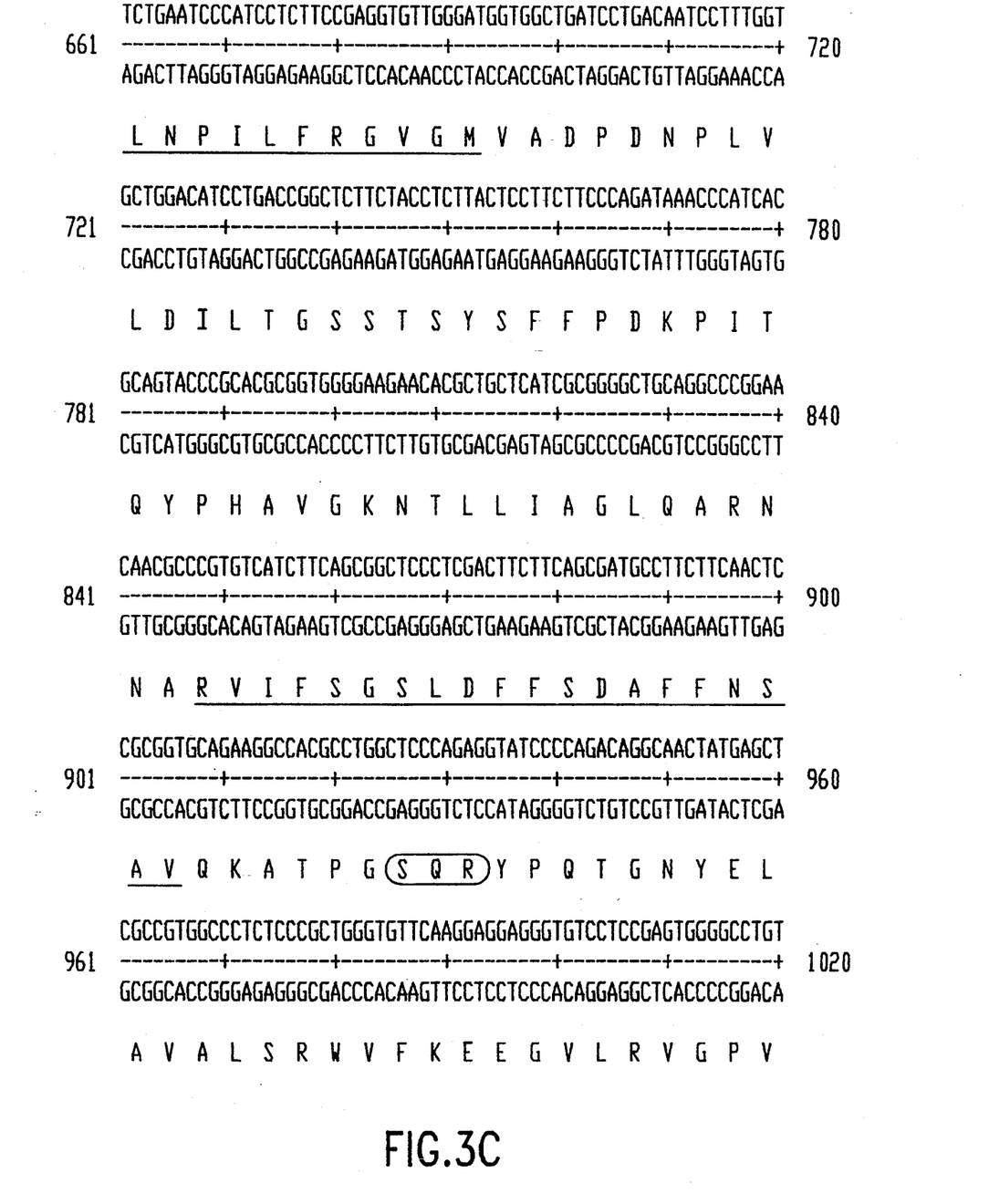
Figure 3D:
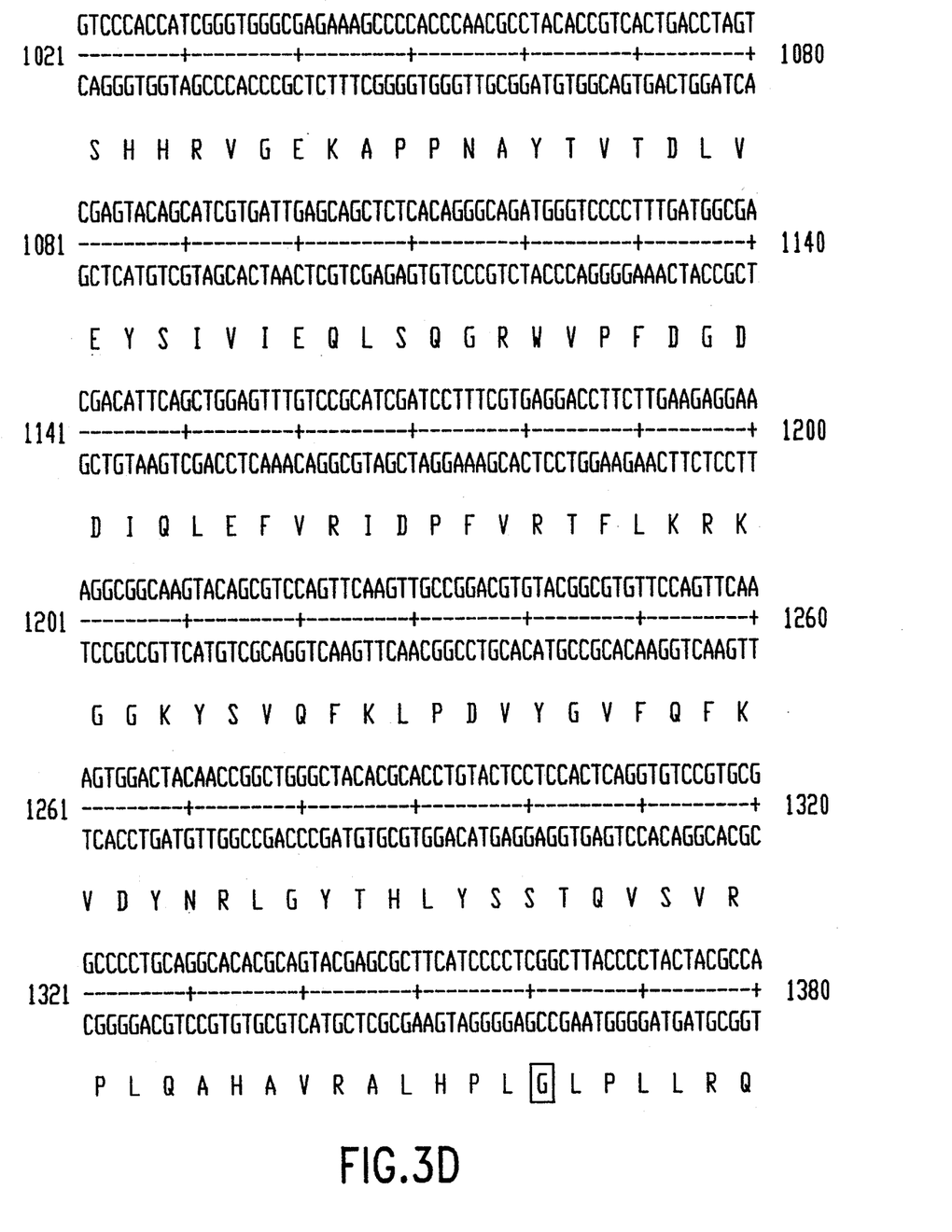

The present invention relates to a nucleic acid fragment comprising a sequence encoding an apamin receptor, as well as the recombinantly produced apamin receptor per se. Such receptors are associated with calcium activated potassium channels in a variety of animal tissues, such as brain, skeletal, cardiac, vascular smooth muscle, pancreas, kidney and liver tissue. An exemplary sequence of Kcal 1.8, a porcine receptor, is provided in FIG. 3A; however, the invention also encompasses any nucleotide sequence which hybridizes, under medium or high stringency conditions (as defined in the Examples below), with a nucleotide sequence encoding the amino acid sequence of FIG. 3A, as well as the biologically active proteins and fragments encoded by such sequences. By "biologically active" is meant proteins or fragments which are capable of eliciting production of antibodies capable of binding to the receptor, as well as proteins or fragments which are associated with calcium activated K+ channels (such as "BK" or "IK") but do not necessarily bind apamin.

The invention also relates to host cells and recombinant vectors useful in expressing the apamin receptor gene and protein. Such hosts will provide a convenient basis for development of screens designed to identify compounds which are capable of modulating activity of the receptor and thus, modulate the activity of the potassium channel. In the heart, modulation of this channel provides a means for regulating an arrhythmic heart; thus, any drug that can open or close this potassium channel is considered a potential antiarrhythmic agent. Similarly, in vascular smooth muscle cells, such as those in veins and arteries, activation of the potassium channel results in hyperpolarization of the smooth muscle membrane, which in turn results in the inhibition of the voltage-gated calcium channels. The inhibition of the latter will then lead to relaxation of the blood vessels and lowering of blood pressure. The receptor is also associated with cognition functions. As noted above, receptor density decreases in Alzheimer's patients, and is involved in the process of learning and memory. Thus, compounds which activate the receptor may be useful in improving impaired cognitive function in Alzheimer's patients, or to enhance memory and learning capacity. Therefore, a convenient system enabling the detection of compounds that modulate potassium channel activity has the potential for identifying drugs with tremendous therapeutic utility. Also, the isolated nucleic acid sequence detectably labelled can be used as a diagnostic probe for Alzheimer's disease, by determining the level of expression of such receptors in peripheral neurons of individuals suspected of being affected. Copending and cofiled applications which have as common inventors Mohammad Reza Ziai and Patricia Tyson Sokol, relating to purified apamin binding proteins Ser. No. 07/922,307, and affinity matrix for binding protein purification Ser. No. 07/922,604 abandoned in favor of Ser. No. 08/144,210, are each incorporated herein by reference in their entirety.

BRIEF DESCRIPTION OF THE FIGURES

FIG. 1 Northern blotting of the mRNA encoding the apamin receptor.
  (A) Poly A+-mRNA isolated from adult rat brain (lane 1), or bovine brain (lane 2) or porcine brain (lane 3) are separated on a denaturing agarose gel, blotted onto nitrocellulose, hybridized with $^{32}$P-labelled Kcal 1.6 cDNA and autoradiographed.
  (B) Poly A+-mRNA isolated from the neonatal rat brain are separated on a denaturing agarose gel, blotted onto nitrocellulose, hybridized with $^{32}$P-labelled Kcal 1.6 cDNA and autoradiographed. The arrows indicate the size (in kilobases) of the two hybridized mRNA bands.

FIG. 3
  (A-E) The nucleotide sequence (SEQ ID NO. 1) and its amino acid translation (SEQ ID NO. 2) of Kcal-1.8 cDNA. The underlined amino acids indicate the potential transmembrane domains of the protein. The oval represents the potential site for protein kinase C. The (*) indicate amino acids which form a potential calcium binding site.
  (F) The hydropathy plot for the protein encoded by Kcal-1.8 cDNA. The four putative but strong hydrophobic domains are indicated by arrows.

DETAILED DESCRIPTION OF THE VECTOR

A full-length apamin binding protein nucleic acid sequence, presumed to be associated with a calcium activated K+ channel, is first isolated from a porcine vascular smooth muscle (aorta) expression cDNA library in a λ-ZAP vector. The library is screened with polyclonal sera raised against a bovine brain apamin receptor. Screening of about 2 million plaque forming units yields four positive plaques which are rescreened and plaque purified.

Figure 1A:
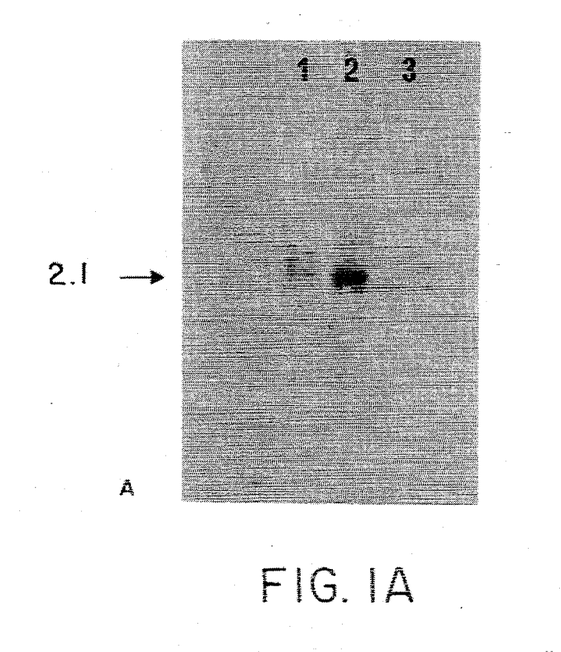
Figure 1B:
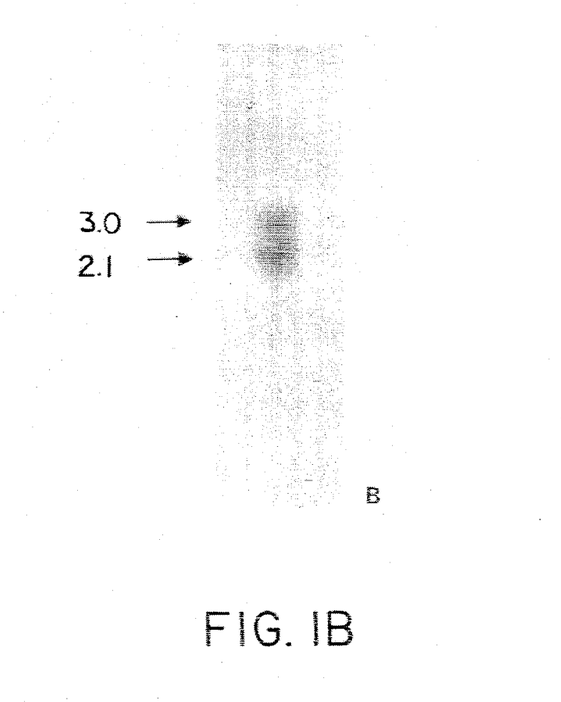

The λ-ZAP is transformed into "pBluescript" plasmid by standard techniques, the DNA is digested with the restriction endonucleases EcoRI and XhoI to release the cDNA inserts and analyzed by agarose gel electrophoresis. One 1.6 Kb cDNA clone (designated Kcal 1.6) is selected for Northern hybridization, genomic Southern blotting and DNA sequencing. As shown in FIG. 1A, the cDNA Kcal 1.6 detects a single mRNA band of approximately 2.1 Kb in the adult rat brain mRNA (lane 1), bovine brain mRNA (lane 2) and porcine brain mRNA (lane 3). The probe, however, reveals two mRNA bands of 2.1 and 3.0 Kb in size in the Northern blot of mRNA from neonatal rat brain (FIG. 1B). These results suggest that in the neonatal rat brain, there are two distinct mRNA species which hybridize to Kcal 1.6, possibly arising by the alternate splicing of mRNA.

Figure 2:
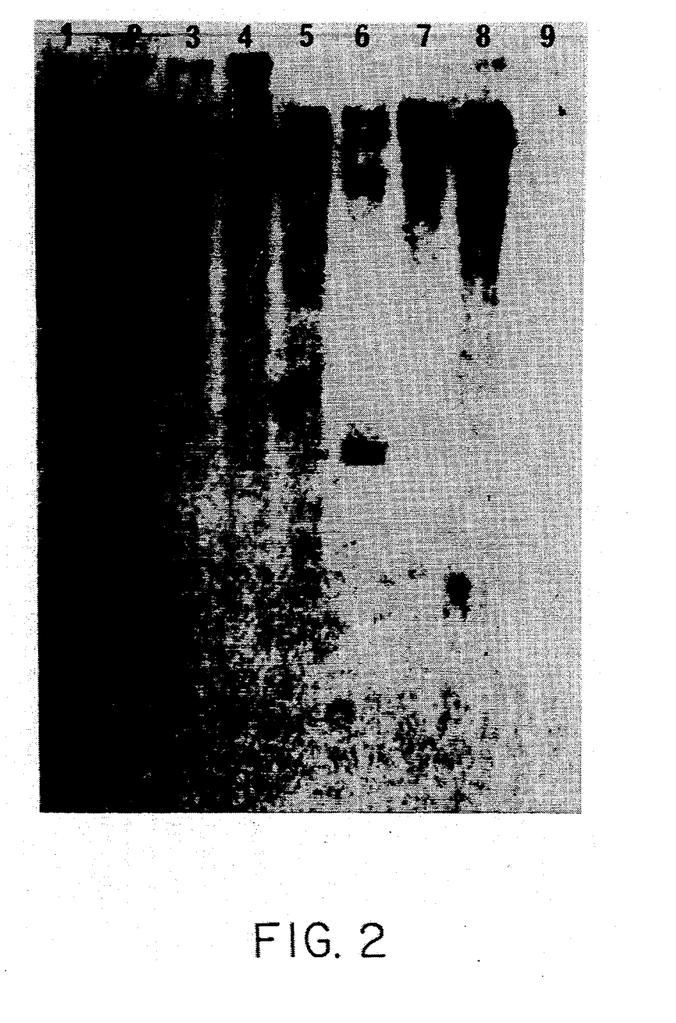
FIG. 2 Genomic Southern hybridization analysis of Kcal 1.6. EcoRI cut-genomic DNA from human (lane 1), monkey (lane 2), rat (lane 3), mouse (lane 4), dog (lane 5), cow (lane 6), rabbit (lane 7), chicken (lane 8) and yeast (lane 9) are hybridized with $^{32}$P-labelled Kcal 1.6 cDNA and autoradiographed.

Next, an EcoRI cut-genomic Southern blot is probed with Kcal 1.6 cDNA. As shown in FIG. 2, after repeated washing of the blot at high stringency, the Kcal 1.6 probe detects a single 14 Kb band in human (lane 1) and in monkey (lane 2). However, there are variable patterns of hybridization in the rat (lane 3), mouse (lane 4), canine (lane 5), bovine (lane 6), rabbit (lane 7) and chicken (lane 8). There is no detectable hybridization with the yeast DNA (lane 9). This experiment indicates that there are significant sequence homologies among the genes encoding p80 in various species. Furthermore, the gene(s) encoding p80 in human and monkey are probably more similar than those in other species.

Figure 3E:
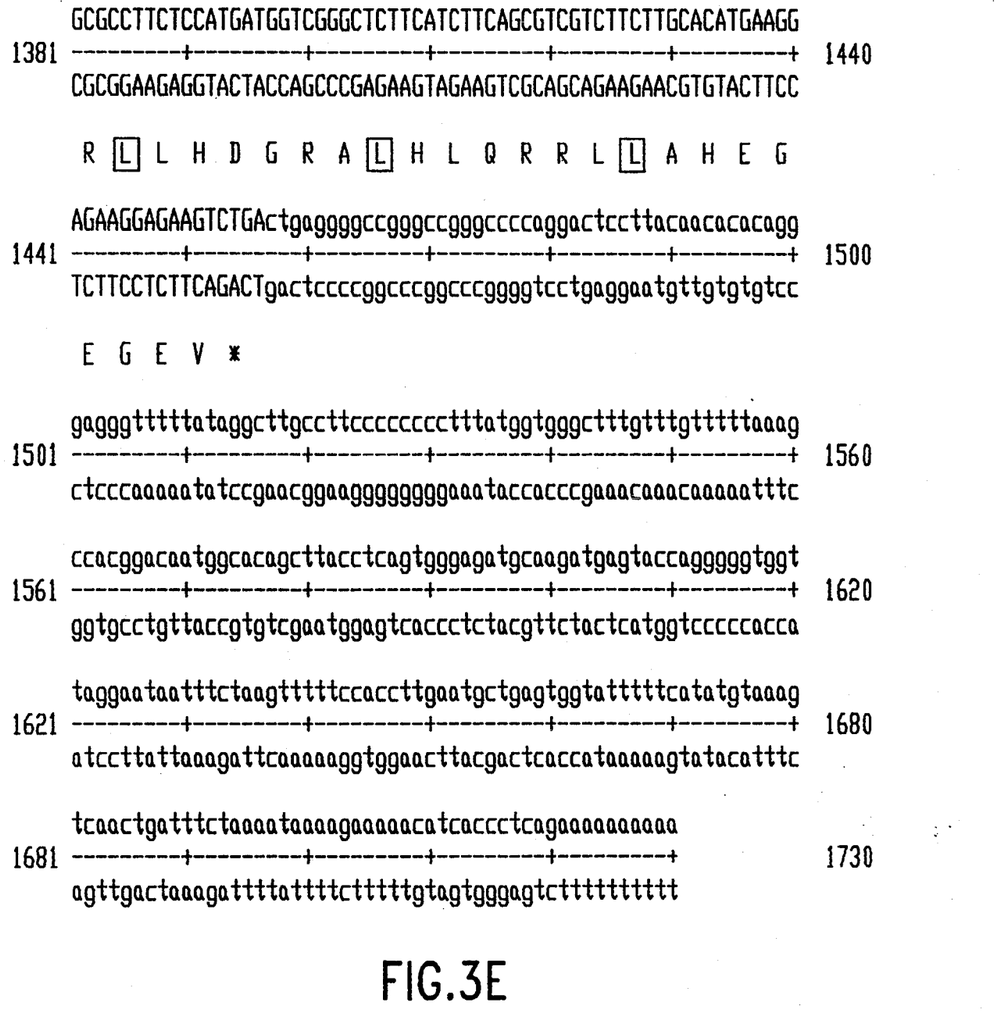
Figure 3F:
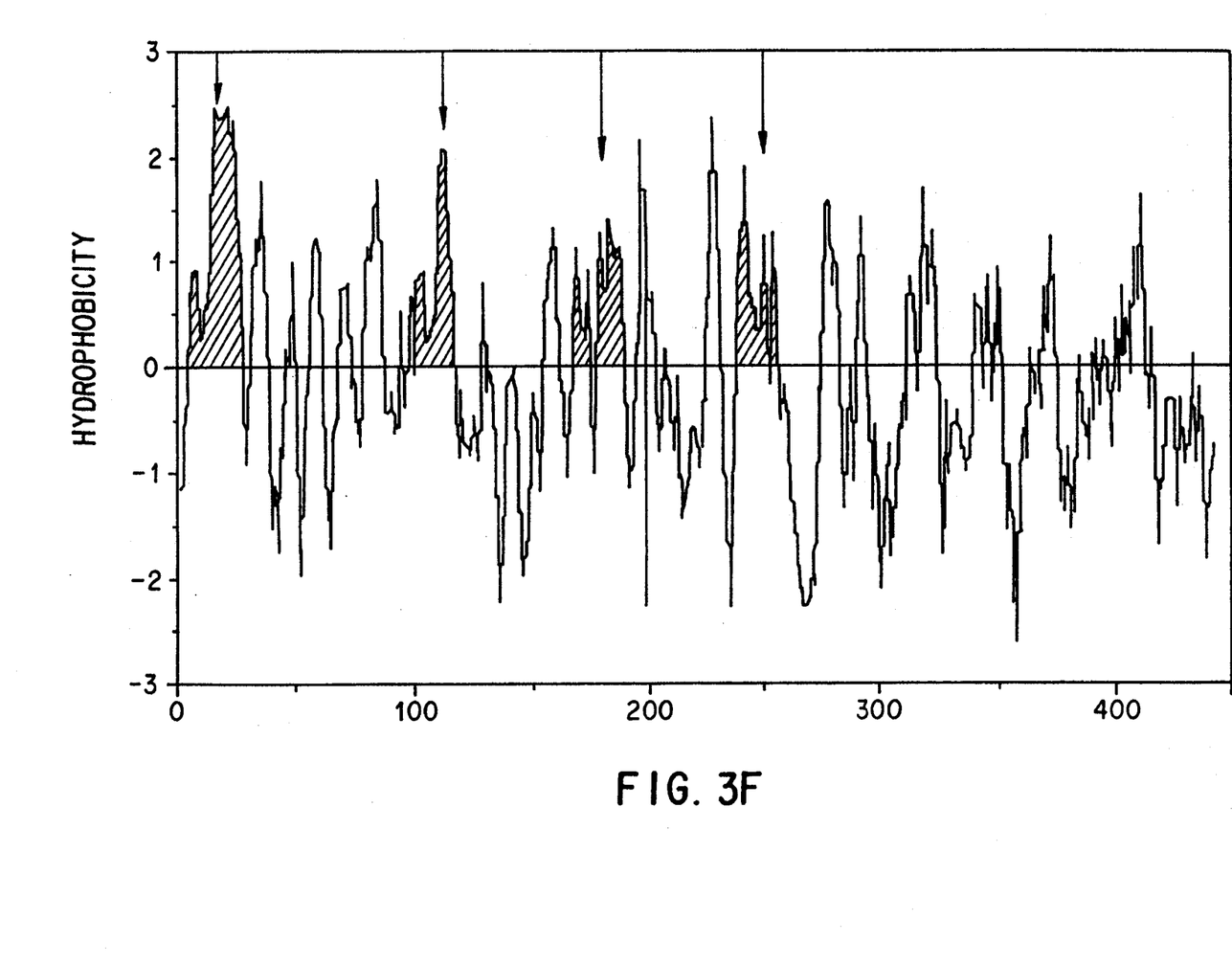

Kcal 1.6 cDNA is then sequenced. The nucleotide sequence obtained indicates that the clone is not of full length and lacks the initiation methionine residue. To obtain a full-length clone, Kcal 1.6 is used as a probe and the original porcine aorta cDNA library is screened, and positive clones analyzed by restriction mapping and electrophoresis for relatedness and insert size. One cDNA clone (designated Kcal 1.8), which appears to be slightly longer than Kcal 1.6, is selected and sequenced by a Taq polymerase sequencing technique. When the nucleotide sequence is translated in frame, the cDNA Kcal 1.8 encodes a protein of 437 amino acids (FIGS. 3A-E), with an initiation methionine and a stop site. Hydrophobicity analysis (FIG. 3F) of the sequence indicates the presence of four strongly hydrophobic putative transmembrane domains (TMD1-4), a short amino terminus and a long carboxyl terminus. The sequence has some interesting features. It contains a strong "EF-Hand" consensus sequence (in FIG. 3E, indicated by a *). The EF-Hand consensus sequence is present in virtually all calcium binding protein members of calmodulin and troponin C families. In fact, the EF-Hand motif in Kcal 1.8 almost perfectly matches that of calmodulin, as well as a recently cloned component of Drosophila calcium activated K-channel, "Slo" (28). In addition, the sequence flanking the putative "EF-Hand" motif of Kcal 1.8 has significant homology with a number of known calcium binding proteins including troponin C, myosin, calreticulin, PEP-19, and several others. Since the small conductance calcium-activated potassium channel (skca) must have a calcium binding site, it gives further support to the belief that Kcal 1.8 indeed encodes skca. If the "EF-Hand" motif is in fact a calcium binding site of Kcal 1.8 protein, it places the "EF-Hand" motif on the cytoplasmic side of the membrane. The amino acid sequence of Kcal 1.8 also contains one protein kinase C site, and one tyrosine kinase phosphorylation site (not shown). In addition, a "leucine zipper" motif can be identified in the C-terminal portion of the protein (FIG. 3E, boxed "L"). At present, the significance, if any, of this motif in Kcal 1.8 is unclear. However, the presence of these putative phosphorylation sites, together with the "EF-Hand" motif are likely to place both N- and C-termini of the protein in the cytoplasmic side of the plasma membrane.

To further confirm Kcal 1.8's identity as an apamin receptor, Kcal cDNA is introduced into a stable mammalian expression vector, pRC/CMV, which is used to transfect CV-1 cells (African green monkey kidney). Cells stably expressing the Kcal 1.8 gene product are selected and are contacted with radiolabelled apamin, in the presence or absence of unlabelled apamin. A number of transfectants show enhanced binding of radio-labelled apamin, thereby adding further confirmation of Kcal 1.8's identity.

The foregoing discussion, and the sequences provided in FIGS. 3A–E, relate to a porcine smooth muscle apamin receptor. However, it will be understood that the invention encompasses more than the specific exemplary sequences. Modifications to the sequence, such as deletions, insertions, or substitutions in the sequence which produce silent changes in the resulting protein molecule are also contemplated. For example, alteration in the gene sequence which reflect the degeneracy of the genetic code, or which result in the production of a chemically equivalent amino acid at a given site, are contemplated; thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a biologically equivalent product. Nucleotide changes which result in alteration of the N-terminal and C-terminal portions of the protein molecule would also not be expected to alter the activity of the protein. It may also be desirable to eliminate one or more of the cysteines present in the sequence, as the presence of cysteines may result in the undesirable formation of multimers when the protein is produced recombinantly, thereby complicating the purification and crystallization processes. In some cases, it may in fact be desirable to make mutants of the sequence in order to study the effect of alteration on the biological activity of the protein. Each of the proposed modifications is well within the routine skill in the art, as is determination of retention of biological activity of the encoded products.

The invention also encompasses homologous sequences obtained from other species and other tissues. As has already been demonstrated above, the nucleic acid sequence depicted in FIGS. 3A–E hybridizes, under relatively stringent conditions, with nucleic acid fragments present in a number of other species, including human, thus demonstrating the ability to isolate other non-porcine sequences. Moreover, apamin receptors from tissue types other than vascular smooth muscle are also known to exist. Brain, skeletal muscle, and liver, in addition to vascular smooth muscle, have been repeatedly demonstrated to express a single class of binding site (4, 15–20). On the other hand, cardiac tissue seems to exhibit a heterogeneous population of target sites. The sequence disclosed in FIGS. 3A–E can thus be used as a probe to isolate the corresponding receptors from other species and tissues. Alternate receptor types are isolatable as follows. cDNA libraries prepared from mRNA from the specific tissue type of interest are probed with radiolabelled Kcal 1.8 cDNA and washed under medium stringency (e.g., 1×SSC, 0.1% SDS, 55° C.). Plaques which appear positive are rescreened to verify authenticity. The positive plaques are then used in plasmid rescue according to techniques known in the art. Rescued plasmids are purified, cut with appropriate restriction enzymes, and analyzed in an agarose gel stained with ethidium bromide. The second gel is transferred to an nitrocellulose filter, probed with labelled Kcal 1.8, washed sequentially under a medium, then high stringency (0.1×SSC, 0.1% SDS, at 65° C.) wash and exposed to X-ray film. Those inserts which strongly hybridize to Kcal 1.8 under high stringency conditions represent likely receptor cDNA candidates. Further confirmation of the identity of these putative receptors can be accomplished according to the protocols described in the following examples, or in accordance with routine techniques known in the art. Thus, the invention encompasses not only the nucleotide and amino acid sequences depicted in FIGS. 3A–E, but also nucleotide sequences which hybridize, under medium or high stringency conditions, with nucleotide sequence encoding the amino acid sequence of FIGS. 3A–E, as well as the biologically active proteins or fragments encoded thereby.

The nucleic acid sequence can be used to express the receptor protein in a variety of host cells, both prokaryotic and eukaryotic for the chosen cell line. Examples of suitable eukaryotic cells include mammalian cells, plant cells, yeast cells, and insect cells. Suitable prokaryotic hosts include *Escherichia coli* and *Bacillus subtills*.

Suitable expression vectors are selected based upon the choice of host cell. Numerous vectors suitable for use in transforming bacterial cells are well known. For example, plasmids and bacteriophages, such as λ phage, are the most commonly used vectors for bacterial hosts, and for *E. coli* in particular. In both mammalian and insect cells, virus vectors are frequently used to obtain expression of exogenous DNA. In particular, mammalian cells are commonly transformed with SV40, polyoma virus, or transfected with plasmids such as pRC/CMV; and insect cells in culture may be transformed with baculovirus expression vectors. Yeast vector systems include yeast centromere plasmids, yeast episomal plasmids and yeast integrating plasmids. The invention encompasses any and all host cells transformed or transfected by the claimed nucleic acid fragments, as well as expression vectors used to achieve this. In particular, the host cells chosen for transfection are cells which exhibit only low (i.e., background) levels of receptor expression (e.g., see FIG. 4) before transcription.

In a preferred embodiment, nucleic acid sequences encoding an apamin receptor are used to transfect eukaryotic cells, preferably mammalian cells. For an initial determination of the ability of a given sequence to produce an apamin binding protein, transient expression, using plasmids such as pcDNAI or PSG5 into which the putative receptor DNA sequence has been ligated, and CMT-1 or COS-1 or -7 cells, can be employed. CMT-1 cells are transfected using the calcium phosphate precipitation method, and within 24 hours of transfection, the SV40 large T antigert is induced with addition of zinc to the medium. Seventy-two hours after transfection, cells are harvested for either RNA isolation or apamin binding assays. Expression is compared between cDNA and mock-transfected cells to determine if receptor activity is achieved by transfected cells. A positive host cell is preferably one which exhibits about twice the background level of apamin binding observed in non-transfected host cells of the same type.

For use of the sequences in screen development, stable expression of the DNA may be desirable. In this case, the DNA encoding the receptor is ligated into a stable vector containing a selectable marker, such as pRC/CMV, pcDNAI Neo, pXTI, or pMAM Neo. The plasmid DNA is linearized and introduced into an appropriate cell line for such vectors, e.g., CV-1, CHO, HEepG-2 or NIH3T3 cells, by electroporation. Successfully transfected cells are identified by selection and isolated clones are picked and amplified. To determine transcription of Kcal message, cellular RNA is isolated and separated electrophoretically on agarose gel. Detection of endogenous and exogenous mRNA is accomplished using Kcal 1.8 as a probe.

Identification of exogenous (transfected) mRNA is accomplished by probing with a 400 bp fragment from the 5' untranslated region of cDNA, since this region is most divergent among species, diminishing the incidence of cross-hybridization.

The ability of any given isolated DNA sequence to yield a functional apamin receptor is determinable by a simple apamin binding assay. Transfected cells are prepared as previously described (41). Binding assays are performed by a standard procedure (16), and values for maximum binding of ligand to receptor (Bmax) and dissociation constant (Kd) for each cell line is calculated.

Further evaluation of the measurement of potassium channel activity in cultured transfectant cells is accomplished by $^{86}$Rb efflux assay (30, incorporated herein by reference). Briefly, stably transfected cells are loaded overnight with $^{86}$Rb in microtiter plates; the medium is then discarded and adherent cells washed three times to remove isotope. Cells are then incubated for 30 minutes at 37° C. with an isotonic buffer containing 20 mM $CaCl_2$ and 100 $\mu$M calcium ionophore A23187. The supernatants from wells are recovered and counted. The cell layer is solubilized in Triton X-100 and also counted, and the percent efflux of $^{86}$Rb calculated as described. The experiment is carried out in the presence or absence of 1 mM apamin (an sKca blocker) or 1 $\mu$M charybdotoxin (a BKca blocker), and control experiments carried out in parallel with cells being incubated with buffer, but without added ionophore. The percent efflux in transfectants harboring cloned DNA mock transfectants, and wild-type CV-1 cells (to measure endogenous efflux) are compared. Such assays are also useful in determining the effect of structural change in the channel in its function, and also to evaluate functional differences between different receptor subtypes. This assay is useful both in confirming activity of a putative receptor/channel as well as confirming the effects

DEPOSIT OF BIOLOGICAL MATERIALS

The following biological materials were deposited with the American Type Culture Collection, 12301 Parklawn Drive, Rockville, Md., on Jun. 18, 1992, and given the Accession Numbers indicated:

| Material | Accession No. |
|---|---|
| E. coli containing | ATCC 69017 |
| pBluescript plasmid containing Kcal 1.8 | |

The present invention is further illustrated by the following non-limiting examples.

EXAMPLES

1. Screening Expression Library

A porcine aorta expression cDNA library in λ-Uni ZAP λR (Stratagene, La Jolla, Calif.) is probed with a 1:1000 dilution of a murine anti-apamin binding protein polyclonal antiserum (M2) using the Vectastain ABC kit (Vector Laboratories Inc., Burlingame, Calif.) as the secondary antibody and detection system. Approximately $2 \times 10^6$ plaque forming units are screened in this manner.

Four positive plaques are selected from the first round of screening. These are subjected to a re-screen and plasmids (pBluescript) containing the cDNA inserts are rescued using a helper phage. The parent plasmid DNA is digested with the restriction endonucleases EcoRI and XhoI to release the cDNA inserts and analyzed by agarose gel electrophoresis. One 1.6 Kb cDNA clone (designated Kcal 1.6) is selected for Northern hybridization, genomic Southern blotting and DNA sequencing. For Northern hybridization, polyA mRNA is isolated from frozen rat tissues using "Fast Track" mRNA isolation kit (Invitrogen, San Diego, Calif.) or purchased from Clontech Labs (Palo Alto, Calif.). Genomic Southern blot, "Zoo-blot" is purchased from Clontech Labs and processed as described by the manufacturer. As shown in FIG. 1A, the cDNA Kcal 1.6 detects a single mRNA band of approximately 2.1 Kb in the adult rat brain mRNA (lane 1) bovine brain mRNA (lane 2) and porcine brain mRNA (lane 3). The probe, however, reveals two mRNA bands of 2.1 and 3.0 Kb in size in the northern blot of mRNA from neonatal rat brain (FIG. 1B). These results may indicate that in the neonatal rat brain, there are two distinct mRNA species which hybridize to Kcal 1.6, possibly arising from the alternate splicing of mRNA. Next, an EcoRI cut-genomic southern blot is probed with Kcal 1.6 cDNA. As shown in FIG. 2, after repeated washing of the blot at high stringency, the Kcal 1.6 probe detects a single 14 Kb band in human (lane 1) and in monkey (lane 2). However, there are variable patterns of hybridization in the rat (lane 3), mouse (lane 4), canine (lane 5), bovine (lane 6), rabbit (lane 7) and chicken (lane 8) ranging from 14 Kb to 3.0 Kb. There is no detectable hybridization with the yeast DNA (lane 9). These results indicate that there are notable homologies among the genes encoding p80 in various species.

2. Sequencing of Kcal 1.6

DNA sequencing is performed using the "Taq-Track" sequencing system (Promega Corp.) or the "Sequenase" system (U.S. Biochemical, Cleveland, Ohio). The nucleotide sequence obtained indicates that the clone is not full length, and lacks an initiation methionine residue. To obtain a full-length clone, Kcal 1.6 is used as a probe to screen the original porcine aorta cDNA library. Positive clones are analyzed by restriction mapping and electrophoresis for relatedness and insert size. One cDNA clone (designated Kcal 1.8) which is slightly longer than Kcal 1.6 is isolated and sequenced. The nucleotide and amino acid sequence of Kcal 1.8 is shown in FIGS. 3A–E. The cDNA encodes 437 amino acids, the hydropathy plot (FIG. 3F) indicates four strongly hydrophobic putative transmembrane domains. There is a putative calcium binding domain which closely matches that of the cloned cDNA slo encoding a putative calcium activated K-channel in Drosophila. However, there is no significant sequence homology between Kcal 1.8 and slo in other regions.

There is one strong consensus sequence in Kcal 1.8 for the cAMP dependent protein kinase, as well as those putative casein kinase phosphorylation sites. The Kcal 1.8 sequence has no significant homologies with any known voltage gated K-channels, sodium channels or calcium channels.

3. Expression of Kcal 1.8

CV-1 cells (ATCC CCL70) stably expressing the Kcal 1.8 gene product are produced by introducing the cDNA in the stable mammalian expression plasmid, pRc/CMV (InVitrogen) which contains a Neo$^r$ marker. The Kcal 1.8 sequence is extracted from the pBluescript vector by digestion, with EcoRI and XhoI, and ligated into the corresponding sites of pRc/CMV. To transfect the cells, confluent 100 mm dishes of CV-1 cells are split and replated the day before the transfection, to ensure the cells are in log-growth phase. For electropotation, cells are harvested with trypsin, washed once with phosphate-buffered saline, and twice with an isotonic, low ionic strength buffer containing 272 mM sucrose, 7 mM sodium phosphate, pH 7.4 and 1 mM MgCl$_2$ (buffer E). The cells are resuspended in this same buffer to a final concentration of $1.5 \times 10^6$ cells/ml. Twenty $\mu$g of the appropriate vector are digested with 40 units of ScaI for 2 hours at 37° C. to linearize the plasmid. The linearized plasmid is phenol/chloroform extracted, EtOH precipitated, and resuspended in 400 $\mu$l of Buffer E. The resuspended DNA is mixed with 400 ul of Cv-1 cells ($1 \times 10^6$ cells) and incubated at room temperature for 2 minutes prior to electroporation. Electroporation is accomplished using a Bio-Rad gene pulser with a 300-V pulse at 25 $\mu$Farads. Transfections are done in duplicate. The suspension is allowed to further incubate for 5 minutes at room temperature, and then plated onto 100 mm tissue culture dishes with 10 mls of Dulbecco's modified Eagle's medium containing 10% fetal calf serum. Two days following transfection, G418 is added to a final concentration of 200 ug/ml. When isolated G418-resistant colonies are identified, they are selected with cloning cylinders and amplified.

Transfected cells are harvested and washed. They are incubated with [$^{125}$I]apamin in the binding buffer "B": Tris-HCl 10 mM, KCl 10 mM, pH 7.4, in the presence or absence of 1 uM cold apamin. The incubation is at 4° C. for 30 minutes with cold apamin, followed by 1 hour incubation at 4° C. with [$^{125}$I]apamin (20,000 cpm/well). Target cells are then filtered and washed with the binding buffer plus BSA. The filters are counted in a gamma counter.

Figure 4:
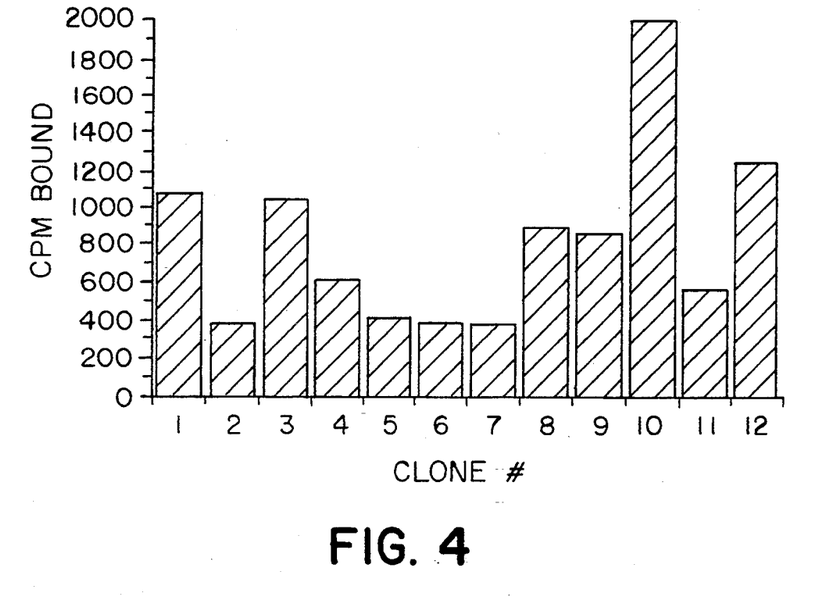
FIG. 4 Binding of apamin to plasma membrane of CV-1 cells transfected with Kcal-1.8 cDNA in a pRC/CMV vector.

As shown in FIG. 4, Transfectant #1, 3, 10 and 12 show significantly enhanced binding of [$^{125}$I]apamin, compared to other transfectants shown.

---

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1730 base pairs
        ( B ) TYPE: nucleic acid
        ( C ) STRANDEDNESS: single
        ( D ) TOPOLOGY: linear     ( i i ) MOLECULE TYPE: cDNA     ( i i i ) HYPOTHETICAL: NO     ( i v ) ANTI-SENSE: NO     ( v i ) ORIGINAL SOURCE:
        ( A ) ORGANISM: Pig     ( i x ) FEATURE:
        ( A ) NAME/KEY: CDS
        ( B ) LOCATION: 140..1456

( x i ) SEQUENCE DESCRIPTION: SEQ ID NO:1:

```
AGCAGCTCCA  TAGGCCCAGC  CCCGGCGTAC  AAGGATCACT  TCCGGTGGTA  CTTCACTACC                    60

AAGAAGCTGC  GATTGGGCGA  GCGTGGAAGG  GGCATTTCCG  GTGTCCACCT  GCTTGGGTTC                   120

TTTGGACAGA  AGTAGGAAG  ATG  GAG  CTC  GGC  GCC  GCG  GCC  CGT  GCT  TGG  TCG            172
                        Met  Glu  Leu  Gly  Ala  Ala  Ala  Arg  Ala  Trp  Ser
                         1                  5                            10

CTC  TTG  TGG  CTG  CTG  CTT  CCC  TTG  CTT  GGC  CTG  GTC  GGC  GCC  AGC  GGT          220
Leu  Leu  Trp  Leu  Leu  Leu  Pro  Leu  Leu  Gly  Leu  Val  Gly  Ala  Ser  Gly
              15                        20                       25

CCC  CGT  ACC  TTA  GTG  CTT  CTG  GAC  AAC  CTC  AAC  CTG  CGG  GAG  ACG  CAT          268
```

-continued

|     |     |     | Pro | Arg | Thr 30 | Leu | Val | Leu | Leu | Asp 35 | Asn | Leu | Asn | Leu | Arg 40 | Glu | Thr | His |     |
|-----|-----|-----|-----|-----|--------|-----|-----|-----|-----|--------|-----|-----|-----|-----|--------|-----|-----|-----|-----|
| TCA | CTT | TTC | TTC | CGG | AGC    | CTA | AAG | GAT | CGG | GGC    | TTC | GTA | CTC | ACA | TTC    |     |     |     | 316 |
| Ser | Leu 45 | Phe | Phe | Arg | Ser | Leu 50 | Lys | Asp | Arg | Gly | Phe 55 | Val | Leu | Thr | Phe |     |     |     |     |
| AAG | ACC | GCA | GAT | GAC | CCC    | AGC | CTG | TCC | CTG | ATT    | AAG | TAC | GGA | GAG | TTC    |     |     |     | 364 |
| Lys 60 | Thr | Ala | Asp | Asp | Pro 65 | Ser | Leu | Ser | Leu | Ile 70 | Lys | Tyr | Gly | Glu | Phe 75 |     |     |     |     |
| CTC | TAT | GAC | AAT | CTC | ATC    | GTC | TTT | TCA | CCT | TCG    | GTA | GAA | GAT | TTT | GGA    |     |     |     | 412 |
| Leu | Tyr | Asp | Asn | Leu 80 | Ile | Val | Phe | Ser | Pro 85 | Ser | Val | Glu | Asp | Phe 90 | Gly |     |     |     |     |
| GGA | AAT | ATC | AAC | GTG | GAG    | ACC | ATC | AGT | ACC | TTT    | ATC | GAC | GGC | GGA | GGC    |     |     |     | 460 |
| Gly | Asn | Ile | Asn 95 | Val | Glu | Thr | Ile | Ser 100 | Thr | Phe | Ile | Asp | Gly 105 | Gly | Gly |     |     |     |     |
| AGT | GTC | CTG | GTA | GCT | GCC    | AGC | TCA | GAC | ATC | GGT    | GAC | CCT | CTC | CGC | GAG    |     |     |     | 508 |
| Ser | Val | Leu 110 | Val | Ala | Ala | Ser | Ser 115 | Asp | Ile | Gly | Asp 120 | Pro | Leu | Arg | Glu |     |     |     |     |
| CTG | GGC | AGT | GAG | TGT | GGG    | ATT | GAG | TTT | GAC | GAG    | GAG | AAA | ACG | GCC | GTC    |     |     |     | 556 |
| Leu | Gly | Ser 125 | Glu | Cys | Gly | Ile 130 | Glu | Phe | Asp | Glu | Glu 135 | Lys | Thr | Ala | Val |     |     |     |     |
| ATT | GAC | CAT | CAC | AAC | TAT    | GAT | GTC | TCA | GAC | CTC    | GGC | CAG | CAC | ACG | CTC    |     |     |     | 604 |
| Ile 140 | Asp | His | His | Asn | Tyr 145 | Asp | Val | Ser | Asp | Leu 150 | Gly | Gln | His | Thr | Leu 155 |     |     |     |     |
| ATT | GTG | GCC | GAC | ACT | GAG    | AAC | CTG | CTG | AAG | GCC    | CCG | ACC | ATC | GTC | GGG    |     |     |     | 652 |
| Ile | Val | Ala | Asp | Thr 160 | Glu | Asn | Leu | Leu | Lys 165 | Ala | Pro | Thr | Ile | Val 170 | Gly |     |     |     |     |
| AAG | TCA | TCT | CTG | AAT | CCC    | ATC | CTC | TTC | CGA | GGT    | GTT | GGG | ATG | GTG | GCT    |     |     |     | 700 |
| Lys | Ser | Ser | Leu 175 | Asn | Pro | Ile | Leu | Phe 180 | Arg | Gly | Val | Gly | Met 185 | Val | Ala |     |     |     |     |
| GAT | CCT | GAC | AAT | CCT | TTG    | GTG | CTG | GAC | ATC | CTG    | ACC | GGC | TCT | TCT | ACC    |     |     |     | 748 |
| Asp | Pro | Asp 190 | Asn | Pro | Leu | Val | Leu 195 | Asp | Ile | Leu | Thr | Gly 200 | Ser | Ser | Thr |     |     |     |     |
| TCT | TAC | TCC | TTC | TTC | CCA    | GAT | AAA | CCC | ATC | ACG    | CAG | TAC | CCG | CAC | GCG    |     |     |     | 796 |
| Ser | Tyr 205 | Ser | Phe | Phe | Pro | Asp 210 | Lys | Pro | Ile | Thr | Gln 215 | Tyr | Pro | His | Ala |     |     |     |     |
| GTG | GGG | AAG | AAC | ACG | CTG    | CTC | ATC | GCG | GGG | CTG    | CAG | GCC | CGG | AAC | AAC    |     |     |     | 844 |
| Val 220 | Gly | Lys | Asn | Thr | Leu 225 | Leu | Ile | Ala | Gly | Leu 230 | Gln | Ala | Arg | Asn | Asn 235 |     |     |     |     |
| GCC | CGT | GTC | ATC | TTC | AGC    | GGC | TCC | CTC | GAC | TTC    | TTC | AGC | GAT | GCC | TTC    |     |     |     | 892 |
| Ala | Arg | Val | Ile | Phe 240 | Ser | Gly | Ser | Leu | Asp 245 | Phe | Phe | Ser | Asp | Ala 250 | Phe |     |     |     |     |
| TTC | AAC | TCC | GCG | GTG | CAG    | AAG | GCC | ACG | CCT | GGC    | TCC | CAG | AGG | TAT | CCC    |     |     |     | 940 |
| Phe | Asn | Ser | Ala 255 | Val | Gln | Lys | Ala | Thr 260 | Pro | Gly | Ser | Gln | Arg 265 | Tyr | Pro |     |     |     |     |
| CAG | ACA | GGC | AAC | TAT | GAG    | CTC | GCC | GTG | GCC | CTC    | TCC | CGC | TGG | GTG | TTC    |     |     |     | 988 |
| Gln | Thr | Gly | Asn 270 | Tyr | Glu | Leu | Ala | Val 275 | Ala | Leu | Ser | Arg | Trp 280 | Val | Phe |     |     |     |     |
| AAG | GAG | GAG | GGT | GTC | CTC    | CGA | GTG | GGG | CCT | GTG    | TCC | CAC | CAT | CGG | GTG    |     |     |     | 1036 |
| Lys | Glu | Glu 285 | Gly | Val | Leu | Arg 290 | Val | Gly | Pro | Val | Ser 295 | His | His | Arg | Val |     |     |     |     |
| GGC | GAG | AAA | GCC | CCA | CCC    | AAC | GCC | TAC | ACC | GTC    | ACT | GAC | CTA | GTC | GAG    |     |     |     | 1084 |
| Gly 300 | Glu | Lys | Ala | Pro | Pro 305 | Asn | Ala | Tyr | Thr | Val 310 | Thr | Asp | Leu | Val | Glu 315 |     |     |     |     |
| TAC | AGC | ATC | GTG | ATT | GAG    | CAG | CTC | TCA | CAG | GGC    | AGA | TGG | GTC | CCC | TTT    |     |     |     | 1132 |
| Tyr | Ser | Ile | Val | Ile 320 | Glu | Gln | Leu | Ser | Gln 325 | Gly | Arg | Trp | Val | Pro 330 | Phe |     |     |     |     |
| GAT | GGC | GAC | GAC | ATT | CAG    | CTG | GAG | TTT | GTC | CGC    | ATC | GAT | CCT | TTC | GTG    |     |     |     | 1180 |
| Asp | Gly | Asp | Asp | Ile 335 | Gln | Leu | Glu | Phe | Val 340 | Arg | Ile | Asp | Pro | Phe 345 | Val |     |     |     |     |
| AGG | ACC | TTC | TTG | AAG | AGG    | AAA | GGC | GGC | AAG | TAC    | AGC | GTC | CAG | TTC | AAG    |     |     |     | 1228 |
| Arg | Thr | Phe | Leu 350 | Lys | Arg | Lys | Gly | Gly 355 | Lys | Tyr | Ser | Val | Gln 360 | Phe | Lys |     |     |     |     |

```
TTG  CCG  GAC  GTG  TAC  GGC  GTG  TTC  CAG  TTC  AAA  GTG  GAC  TAC  AAC  CGG         1276
Leu  Pro  Asp  Val  Tyr  Gly  Val  Phe  Gln  Phe  Lys  Val  Asp  Tyr  Asn  Arg
     365                 370                      375

CTG  GGC  TAC  ACG  CAC  CTG  TAC  TCC  TCC  ACT  CAG  GTG  TCC  GTG  CGG  CCC         1324
Leu  Gly  Tyr  Thr  His  Leu  Tyr  Ser  Ser  Thr  Gln  Val  Ser  Val  Arg  Pro
380                      385                 390                           395

CTG  CAG  GCA  CAC  GCA  GTA  CGA  GCG  CTT  CAT  CCC  CTC  GGC  TTA  CCC  CTA         1372
Leu  Gln  Ala  His  Ala  Val  Arg  Ala  Leu  His  Pro  Leu  Gly  Leu  Pro  Leu
               400                      405                           410

CTA  CGC  CAG  CGC  CTT  CTC  CAT  GAT  GGT  CGG  GCT  CTT  CAT  CTT  CAG  CGT         1420
Leu  Arg  Gln  Arg  Leu  Leu  His  Asp  Gly  Arg  Ala  Leu  His  Leu  Gln  Arg
               415                      420                      425

CGT  CTT  CTT  GCA  CAT  GAA  GGA  GAA  GGA  GAA  GTC  TGACTGAGGG  GCCGGGCCGG          1473
Arg  Leu  Leu  Ala  His  Glu  Gly  Glu  Gly  Glu  Val
               430                      435

GCCCCAGGAC  TCCTTACAAC  ACACAGGGAG  GGTTTTTATA  GGCTTGCCTT  CCCCCCCCTT                 1533

TATGGTGGGC  TTTGTTTGTT  TTTAAAGCCA  CGGACAATGG  CACAGCTTAC  CTCAGTGGGA                 1593

GATGCAAGAT  GAGTACCAGG  GGGTGGTTAG  GAATAATTTC  TAAGTTTTTC  CACCTTGAAT                 1653

GCTGAGTGGT  ATTTTTCATA  TGTAAAGTCA  ACTGATTTCT  AAAATAAAAG  AAAAACATCA                 1713

CCCTCAGAAA  AAAAAAA                                                                    1730

( 2 ) INFORMATION FOR SEQ ID NO:2:

( i ) SEQUENCE CHARACTERISTICS:
        ( A ) LENGTH: 438 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

Met  Glu  Leu  Gly  Ala  Ala  Ala  Arg  Ala  Trp  Ser  Leu  Leu  Trp  Leu  Leu
 1                   5                   10                      15

Leu  Pro  Leu  Leu  Gly  Leu  Val  Gly  Ala  Ser  Gly  Pro  Arg  Thr  Leu  Val
               20                      25                      30

Leu  Leu  Asp  Asn  Leu  Asn  Leu  Arg  Glu  Thr  His  Ser  Leu  Phe  Phe  Arg
               35                      40                      45

Ser  Leu  Lys  Asp  Arg  Gly  Phe  Val  Leu  Thr  Phe  Lys  Thr  Ala  Asp  Asp
          50                      55                      60

Pro  Ser  Leu  Ser  Leu  Ile  Lys  Tyr  Gly  Glu  Phe  Leu  Tyr  Asp  Asn  Leu
 65                      70                      75                      80

Ile  Val  Phe  Ser  Pro  Ser  Val  Glu  Asp  Phe  Gly  Gly  Asn  Ile  Asn  Val
                    85                      90                      95

Glu  Thr  Ile  Ser  Thr  Phe  Ile  Asp  Gly  Gly  Ser  Val  Leu  Val  Ala
                    100                     105                     110

Ala  Ser  Ser  Asp  Ile  Gly  Asp  Pro  Leu  Arg  Glu  Leu  Gly  Ser  Glu  Cys
               115                     120                     125

Gly  Ile  Glu  Phe  Asp  Glu  Glu  Lys  Thr  Ala  Val  Ile  Asp  His  His  Asn
          130                     135                     140

Tyr  Asp  Val  Ser  Asp  Leu  Gly  Gln  His  Thr  Leu  Ile  Val  Ala  Asp  Thr
145                     150                     155                     160

Glu  Asn  Leu  Leu  Lys  Ala  Pro  Thr  Ile  Val  Gly  Lys  Ser  Ser  Leu  Asn
               165                     170                     175

Pro  Ile  Leu  Phe  Arg  Gly  Val  Gly  Met  Val  Ala  Asp  Pro  Asp  Asn  Pro
               180                     185                     190

Leu  Val  Leu  Asp  Ile  Leu  Thr  Gly  Ser  Ser  Thr  Ser  Tyr  Ser  Phe  Phe
               195                     200                     205
```

```
Pro  Asp  Lys  Pro  Ile  Thr  Gln  Tyr  Pro  His  Ala  Val  Gly  Lys  Asn  Thr
210                      215                      220

Leu  Leu  Ile  Ala  Gly  Leu  Gln  Ala  Arg  Asn  Asn  Ala  Arg  Val  Ile  Phe
225                      230                      235                      240

Ser  Gly  Ser  Leu  Asp  Phe  Phe  Ser  Asp  Ala  Phe  Phe  Asn  Ser  Ala  Val
               245                      250                      255

Gln  Lys  Ala  Thr  Pro  Gly  Ser  Gln  Arg  Tyr  Pro  Gln  Thr  Gly  Asn  Tyr
               260                      265                      270

Glu  Leu  Ala  Val  Ala  Leu  Ser  Arg  Trp  Val  Phe  Lys  Glu  Glu  Gly  Val
          275                      280                      285

Leu  Arg  Val  Gly  Pro  Val  Ser  His  His  Arg  Val  Gly  Glu  Lys  Ala  Pro
     290                      295                      300

Pro  Asn  Ala  Tyr  Thr  Val  Thr  Asp  Leu  Val  Glu  Tyr  Ser  Ile  Val  Ile
305                      310                      315                      320

Glu  Gln  Leu  Ser  Gln  Gly  Arg  Trp  Val  Pro  Phe  Asp  Gly  Asp  Asp  Ile
               325                      330                      335

Gln  Leu  Glu  Phe  Val  Arg  Ile  Asp  Pro  Phe  Val  Arg  Thr  Phe  Leu  Lys
               340                      345                      350

Arg  Lys  Gly  Gly  Lys  Tyr  Ser  Val  Gln  Phe  Lys  Leu  Pro  Asp  Val  Tyr
          355                      360                      365

Gly  Val  Phe  Gln  Phe  Lys  Val  Asp  Tyr  Asn  Arg  Leu  Gly  Tyr  Thr  His
     370                      375                      380

Leu  Tyr  Ser  Ser  Thr  Gln  Val  Ser  Val  Arg  Pro  Leu  Gln  Ala  His  Ala
385                      390                      395                      400

Val  Arg  Ala  Leu  His  Pro  Leu  Gly  Leu  Pro  Leu  Leu  Arg  Gln  Arg  Leu
               405                      410                      415

Leu  His  Asp  Gly  Arg  Ala  Leu  His  Leu  Gln  Arg  Arg  Leu  Leu  Ala  His
               420                      425                      430

Glu  Gly  Glu  Gly  Glu  Val
          435
```

REFERENCES

1. Rudy, B., *Neuroscience*, 25:729–749, 1988.
2. Halliwell, J. V., In Cook, N. S. (Ed.), *Potassium Channels; Structure, Classification, Function and Therapeutic Potential*, Ellis Horwood Ltd., 348–372, 1990.
3. Castle, N. A., Haylett, D. G., and Jenkinson, D. H., *TINS*, 1259-65, 1989.
4. Haylett, B. G. and D. H. Jenkinson, In Cook, N. S. (Ed.), *Potassium Channels; Structure, Classification, Function and Therapeutic Potential*, Ellis Horwood Ltd., 70–95, 1990.
5. Latorre, R., Oberhauser, A., Labarca, P. and Alvafez, O., *Annu. Rev. Physiol.*, 51:385–399, 1989.
6. Pennefather, P., Lancaster, B., Adams, P. and Nicoll, R. A., *Proc. Nat. Acad. Sci.*, USA 82:3040–3044, 1985.
7. Marty, A., *TINS*, 1.2:420–424, 1989.
8. Lancaster, B., Nicoll, R. A. and Perkel, D. J., *J. Neurosci.*, 11:23–30, 1991.
9. Strong, P. N., *Pharmac. Ther.*, 46137–162, 1990.
10. Saunders, H. H. and Farley, J. M., *J., Pharmacol. Exp. Ther.*, 257:1114–1119, 1991.
11. Moczydlowski, E., Lucchesi, K. and Ravindran, A., *J. Membrane Biol.*, 105:95–111, 1988.
12. Blatz, A. L. and Magleby, K. L., *J. Gen. Physiol.*, 84:1–23, 1984.
13. Blatz, A. L. and Magleby, K. L., *Nature*, 323:718–720, 1986.
14. Blatz, A. L. and Magleby, K. L., *TINS*, 10:463–467, 1987.
15. Habermann, E. and Fischer, K., *Eur. J. Biochem.*, 94:355–364, 1979.
16. Mourre, C., Hugues, M. and Lazdunski, M., *Brain Res.*, 382:239–249, 1986.
17. Seagar, M. J., Labbe-Jullie, C., Granier, C., Goll, A., Glossmann, H., Van Rietschoten, J. and Couraud, F., *Biochemistry*, 25:4051–4057, 1986.
18. Seagar, M. J., Marqueze, B. and Couraud, F., *J. Neurosci.*, 7:565–570, 1987.
19. Schmid-Antomarchi, H., Hugues, M., Norman, R., Ellory, C., Borsotto, M. and Lazdunski, M., *Eur. J. Biochem.*, 1421-6, 1984.
20. Wu, K., Carlin, R., Sachs, L. and Siekevitz, P., *Brain Res.*, 360:183–194, 1985.
21. Seagar, M. J., Labbe-Jullie, C., Granier, C., Van Rietschoten, J., Couraud, F., *J. Biol. Chem.*, 260:3895–3898, 1985.
2. Leveque, C., Marqueze, B., Couraud, F. and Seagar, M., *FEBS Letters*, 275:185–189, 1990.
23. Marqueze, B., Seagar, M. J., Couraud, F., *Eur. J. Biochem*, 169:295–298, 19874.
24. Laemmli, U.K., *Nature*, 227:680–685, 1970.
25. Ziai, M.R., Imberti, L., Nicotra, M.R., Badaracco, G., Segatto, O., Natall, P. G. and Ferrone, S., *Cancer Res.*, 47:2474–2480, 1987.
26. Ziai, M.R., Imberti, L., and Ferrone, S., *Immunol. Methods*, 82:233–241, 1985.

27. Hayashibe, K., Sassano, D., and Ziai, M. R., *J. Immunoassay*, 11:89–95, 1990.
28. Ohandra, M. and Frith, C. H., *Toxicol. Pathol*, 19:164–167, 1991.
29. Staros, J. V., Wright, R. W., and Swingle, D.M, *Analyt. Biochem.*, 156:220–222, 1986.
30. Vaitukatis, J. L., *Methods in Enzymology*, 73:46–52, 1981.
31. Hsu, H. T, Wang, Y. C., Lawson, R. H., Wang, M. and Gonsalves, D., *Phytopathol.*, 80:158–162, 1990.
32. Cornett, W. C., Vincent, J. W., Gray, W. A., and Falkler, Jr., W. A., *J. Immunol. Methods*, 84:321–326, 1985.
33. Zweifach, A., Desir, G. V., Aronson, P. S., and Giebisch, G. H., *Amer. J. Physiol.*, 261:F187–F196, 1991.
34. Laskowski, F. H., Christine, C. W., Gitter, A. H., Beyenbach, K. W., Gross., P. and Froemter, E., *Renal Phys. Biochem.*, 13:70–81, 1990.
35. Cornejo, M., Gurggino, S. E., Guggino, W. B., *J. Membr. Biol.*, 110:49–56, 1989.
36. Klaerke, D. A., Karlish, S. J. D., Jorgenson, P. L., *J. Membr. Biol.*, 95:105–112, 1987.
37. Lu, L., Montrose-Rafizadeh, C. and Giggino, W. B., *J. Biol. Chem.*, 265:16190–16194, 1990.
38. Wang, W., Sackin, H., Giebisch, G., *Annu. Rev. Physiol.*, 54:81–96, 1992.
39. Ikeda, M., Dewar, D. and McCulloch, J., *Brain Res.*, 567:51–56, 1991.
40. Atkinson, N. S, Robertson, G. A. and Ganetzky, B., *Science.*, 253:551–555, 1991.
41. Daniel, S., Malkowitz, L., Wang, H-C, Beer, B. and Ziai, M. R., *J. Pharmacol. Methods*, 25:185–193, 1991.
42. Messier, C., Mourre, C., Bontempi, B., Sif, J., Lazdunski, M. and Destrade, C., *Brain Res.*, 551:322–326, 1991.

What we claim is:

1. A composition consisting essentially of an oligonucleotide encoding porcine apamin binding protein, wherein the oligonucleotide hybridizes under high stringency conditions with a nucleic acid sequence encoding the amino acid sequence of SEQ ID NO. 2.
2. The composition of claim 1, wherein the oligonucleotide encodes binding protein expressed in a porcine tissue selected from the group consisting of brain, heart, smooth muscle, kidney, liver, pancreas and neuron.
3. The composition of claim 1, wherein the oligonucleotide has the sequence of SEQ ID NO. 1.
4. A host cell transformed or transfected with the composition of claim 1.
5. The host cell of claim 4 which binds apamin at about twice the level of the host cell in its untransformed or untransfected state.
6. A recombinant vector comprising the composition of claim 1.
7. The vector of claim 6 wherein the oligonucleotide has the sequence of SEQ ID NO. 1.
8. A host cell comprising the vector of claim 7.

* * * * *